(12) United States Patent
Krug et al.

(10) Patent No.: US 8,557,265 B2
(45) Date of Patent: Oct. 15, 2013

(54) USE OF A SYNERGISTIC COMPOSITION AS A THERAPEUTIC AGENT OF DISINFECTANT

(75) Inventors: Barbara Krug, Hamburg (DE); Sven Eggerstedt, Hamburg (DE); Christiane Ostermeyer, Hamburg (DE); Thomas Lisowsky, Monheim (DE); Karlheinz Esser, Mönchengladbach (DE); Frank Büger, Düsseldorf (DE); Richard Bloss, Rellingen (DE)

(73) Assignee: Bode Chemie GmbH, Hamburg (DE)

( * ) Notice: Subject to any disclaimer, the term of this patent is extended or adjusted under 35 U.S.C. 154(b) by 381 days.

(21) Appl. No.: 12/452,295

(22) PCT Filed: Jun. 27, 2008

(86) PCT No.: PCT/EP2008/005292
§ 371 (c)(1),
(2), (4) Date: Dec. 23, 2009

(87) PCT Pub. No.: WO2009/000551
PCT Pub. Date: Dec. 31, 2008

(65) Prior Publication Data
US 2010/0119566 A1 May 13, 2010

(30) Foreign Application Priority Data
Jun. 28, 2007 (DE) .................. 10 2007 030 103

(51) Int. Cl.
*A01N 25/00* (2006.01)
*A01N 25/02* (2006.01)
*A01N 59/00* (2006.01)
*A61K 9/12* (2006.01)

(52) U.S. Cl.
USPC .................. 424/405; 424/43; 424/600

(58) Field of Classification Search
None
See application file for complete search history.

(56) References Cited

U.S. PATENT DOCUMENTS

| 6,329,343 B1 | 12/2001 | Leung et al. .............. 514/23 |
| 2001/0046533 A1 | 11/2001 | Bailey et al. .............. 426/72 |
| 2003/0185915 A1 | 10/2003 | Carlo et al. ............. 424/744 |
| 2006/0198902 A1 | 9/2006 | Froggatt et al. .......... 424/618 |
| 2007/0077220 A1 | 4/2007 | Ramirez et al. .......... 424/70.1 |
| 2009/0028961 A1* | 1/2009 | Lisowsky et al. .......... 424/617 |

FOREIGN PATENT DOCUMENTS

| DE | 196 03 653 | 8/1997 | ......... H04B 1/04 |
| DE | 19936428 | 2/2000 | ......... A61K 33/26 |
| DE | 10 2005 020 327 | 11/2006 | ......... A01N 59/16 |
| DE | 10 2005 044 361 | 3/2007 | ......... A61F 3/02 |

(Continued)

OTHER PUBLICATIONS

German search report, mailed May 20, 2008, in priority application DE 10 2007 030 103.2 (4 pages).

(Continued)

*Primary Examiner* — Aradhana Sasan
(74) *Attorney, Agent, or Firm* — Nash and Titus, LLC

(57) ABSTRACT

The invention relates to the use of a composition comprising a vitamin, a metal ion, and a surfactant, as a therapeutic agent or disinfectant. The composition has been known as a decontaminant because the same efficiently decomposes DNA. It has now been possible to demonstrate that the agent has surprisingly good compatibility while having a wide-ranging disinfecting effect and is therefore also suitable for other purposes, e.g., for disinfecting or dressing wounds.

14 Claims, 1 Drawing Sheet

(56) References Cited

FOREIGN PATENT DOCUMENTS

| DE | 10 2006 018 983 | 10/2007 | C11D 3/02 |
| DE | 10 2006 049 108 | 4/2008 | C09D 5/14 |
| EP | 0 046 409 | 2/1982 | A61K 31/375 |
| EP | 1 366 768 | 12/2003 | A61K 38/28 |
| FR | 2 041 M | 9/1963 | |
| GB | 2 292 746 | 3/1996 | C11D 3/12 |
| WO | WO 95/15118 | 6/1995 | A61B 8/00 |
| WO | WO 01/55128 | 8/2001 | C07D 307/83 |
| WO | WO 02/28187 | 4/2002 | A01N 59/16 |
| WO | WO2006/116983 | 11/2006 | A01N 59/00 |

OTHER PUBLICATIONS

English abstract for WO2006/116983 (Nov. 9, 2006)(1 page).
English abstract for WO 01/55128 (Aug. 2, 2001)(1 page).

\* cited by examiner

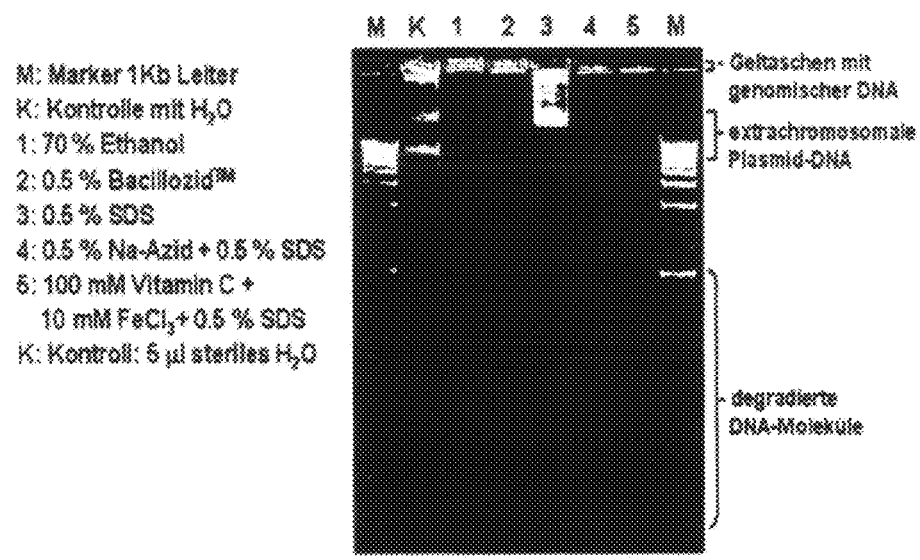

USE OF A SYNERGISTIC COMPOSITION AS A THERAPEUTIC AGENT OF DISINFECTANT

FIELD OF THE INVENTION

The invention concerns new uses of a composition consisting of at least one vitamin, at least one metal ion and at least one surfactant. The invention, moreover, concerns a therapeutic agent or disinfectant comprising at least one active ingredient and the usual substrates and/or adjuvants.

BACKGROUND OF THE INVENTION

In many areas it is necessary to remove biological and organic impurities, such as proteins, DNA and microorganisms, completely from a surface. For this, one often uses so-called decontaminants, which degrade and remove contamination due to proteins and nucleic acids. It is known that not only the microorganisms themselves, but also individual DNA molecules still show an activity and thus can lead to infections or strengthen the infectiousness and pathogenicity of microorganisms. These must therefore be removed by way of DNA decontamination so that a complete destruction or inactivation of the genetic information is achieved. For an efficient decontamination, it is necessary for the free DNA molecules to be modified, denatured, or degraded. Particularly effective decontamination occurs through the most complete DNA breakdown possible. Known decontamination solutions often contain corrosive chemical substances. Thus, for example, sodium hypochlorite or mixtures of surfactants with phosphoric acid or sodium hydroxide or sodium azide are used in products for DNA breakdown for cleaning of surfaces. These corrosive solutions sometimes lead to permanent modifications of the proteins and can produce partially oxidative damage. Therefore, they can only be used for decontamination, i.e., for DNA breakdown on devices, instruments, and work surfaces, and this only on those which consist of materials that are not sensitive to these corrosive chemicals.

The combating of microorganisms is usually done by way of disinfecting. This generally means the effective, irreversible inactivation, killing or removal of microorganisms such as bacteria, mycobacteria, fungi, yeasts, spores, prions and/or viruses from living and lifeless surfaces, tissues/fabrics and rooms. In addition to a disinfecting, a complete DNA breakdown is desirable, especially to prevent resistance. It is precisely in the fields of wound dressing and in many disinfecting applications that a complete breakdown and inactivation of proteins, enzymes, or nucleic acids of harmful microorganisms is expedient. However, this is not possible with the presently known corrosive agents for DNA breakdown, i.e., decontamination.

In wound healing, one uses at present either hydroactive bandages of alginates or polymer foams based on polyurethane or fiber filaments made from biomaterials such as carboxymethyl cellulose or reduced/oxidized cellulose and collagen or their composites. These substrate materials are usually doped with silver ions to achieve a bactericidal or bacteriostatic action and at the same time stabilize the moisture regime in the wound. The functionality is defined in terms of the degree and quantity of moisture and wound debris taken up, and the formulation of the gel formation. Defined properties of silver ion release lead to the desired bactericidism in dependence on the technology used (lamination, embedding, etc.).

The antimicrobial activity of silver has been known for more than 100 years and is presently experiencing a kind of renaissance for wound dressings. For lack of usable alternatives, one also puts up with the drawbacks of silver (in the form of silver ions). Meanwhile, the limits for the use of silver as a bacteriostatic agent are already well known and involve the following points:

Its antimicrobial activity is not equally good for all microorganisms and occurs with a large time lag (oligodynamism of silver).

Silver ions under harsh conditions (high protein content in the wound secretions and high microbial germination) quickly loose their antimicrobial properties, which can only be offset by a higher frequency of bandage change intervals and, thus, higher initial treatment costs.

The passage of silver ions into the blood plasma is unwanted for open wounds, since harmful toxic effects can also occur due to bioavailability of silver.

An increased concentration of silver ions in the blood leads to intensified blood clotting and, thus, risk of thrombosis.

Precipitation of particles due to chloride fractions in the bodily electrolytes leads to argyria. Diagnostic techniques, such as magnetic resonance tomography, cannot be carried out free of risk in wound patients who have been treated with silver wound dressings, since magnetization of the Ag+Cl— particles produces the threat of a dangerous vessel perforation in the arterioles. Only at high chloride concentration does the silver chloride dissolve once more, forming dichloroargentate: $AgCl + Cl^- \leftrightarrows [AgCl2]^-$.

Topical antibiotics have been used for many years in wound dressing, since they are selectively cytotoxic, attack primarily the foreign bacterial cells in the wound, and have only slight effects on human cells. However, the drawbacks are as follows:

Many topical antibiotics are only effective against specific bacteria, but wounds are usually colonized by different types.

The dispensing systems of some antibiotics are often only somewhat useful in supporting other aspects of wound management, such as the carrying away of wound secretion, an increased occurrence of which is often associated with a greater germ population.

Solutions, creams and salves are unable to take up or otherwise manage wound secretion.

In addition, there is the problem of resistance, induced by too frequent use of antibiotics, so that they must often be reserved for a systemic use.

Topical antiseptics have the advantage of having a broadband effect and they can thus combat nearly all species of bacteria. Despite the widespread use, usually no bacterial resistance to topical antiseptics occurs. Some clinicians consider the broadband effect to be a drawback, since the antiseptics do not distinguish between foreign and human cells. Hence, they constitute a potential danger to wound healing. However, most data cited on the harmfulness of antiseptics are based on in vitro studies and not on analysis of the effect on cells in their natural setting (i.e., in tissue). The potential harmful effects of antiseptics on the healing wound are more likely due to their dispensing system than to their chemical action. A current in vivo study demonstrated that antiseptics do not delay wound healing. The typical dispensing system for antiseptics consists of gauze and is generally remoistened once or twice daily. But since antiseptics bind to proteins, they have only a short action time (1 to 2 minutes) in the wound bed. In the wound, the antiseptic can be quickly bound by other protein sources (such as blood, serum, extracellular matrix) and is then no longer available for the killing of bacteria. Moreover, gauze does not preserve an optimally moist wound environment, nor does it constitute a physical obstacle to a secondary colonization by bacteria.

In summary, it can be said that both kinds of antimicrobial substances have their advantages and drawbacks. Local antibiotics are selectively cytotoxic, but have only a narrow action spectrum and promote the occurrence of resistance. Whereas topical antiseptics have a broad action spectrum and the danger of forming resistance is significantly less, they do not act selectively and have only a very short action time and a poor dispensing system.

From DE 10 2005 020 327 A1 and WO 2006/116983 A2, both of which are the foundation of the present invention and their content is therefore also part of the present application, a decontamination solution is known that comprises a synergistic mixture of at least one vitamin, at least one metal ion, and at least one surfactant. This synergistic mixture is used for treatment of surfaces being cleaned. The decontamination solution brings about an inactivation and degradation of proteins and nucleic acids on the surfaces treated, and this action occurs with essentially the same efficiency over the entire pH range of 2 to 8.5. Because one can work at these comparatively mild pH values, this solution is sparing on the surfaces being treated. By spraying on and/or rubbing in the solution or soaking in the solution, proteins and nucleic acids are denatured, solubilized, inactivated, degraded and removed. Thus, the solution exhibits an effective DNA breakdown.

Yet as is known, decontamination solutions are only used for cleaning of lifeless surfaces, such as instruments and object surfaces. Due to their corrosiveness, they are never used in particular when contact can occur with living surfaces, such as skin, hands, or mucous membrane. The decontamination solution described in DE 10 2005 020 327 A1 is therefore used thus far for treatment, i.e., decontamination, of lifeless surfaces.

SUMMARY OF THE INVENTION

The problem of the invention is to open up new areas of application for compositions which contain at least one vitamin, at least one metal ion and at least one surfactant compound. Moreover, it is the problem of the invention to provide a therapeutic agent or disinfectant that avoids the mentioned drawbacks of topical antibiotics and antiseptics, exhibits good skin toleration and material compatibility, and supports and hastens wound healing. Furthermore, an agent should be provided that enables an improvement in wound treatment and a disinfecting, in addition to the decontamination or DNA breakdown.

This problem is solved according to the invention by the use of a composition that consists of at least one vitamin, at least one metal ion and at least one surfactant substance, as an agent for
    wound dressing,
    treatment or prevention of infections,
    disinfecting, or
    disinfective cleansing.

The use of various vitamins (natural antioxidants) in combination with metal ions and detergents leads to extremely fast, massive strand breakages and modifications in nucleic acid molecules and proteins. This effect leads to an efficient inactivation and destruction of the genetic information and proteins, thereby achieving an especially effective decontamination. It has now been shown that, besides the DNA breakdown, surprisingly a broad antimicrobial, antibiotic, antiviral, levurocidal and fungicidal action is also present when using the composition of metal ions, vitamins and detergents. Therefore, a use is also possible for disinfective applications in medicinal or therapeutic applications, especially the disinfecting of wounds, wound treatment and fighting of external infections of the skin, mucous membrane, or wounds. The composition effectively kills germs and thereby disinfects wounds, areas of skin, and tissue. Wound healing is promoted and hastened, while the composition is very well tolerated on account of its ingredients which are harmless to animals and man.

In one embodiment, therefore, the use of the composition according to the invention is for wound dressing. Especially preferably, the composition according to the invention is used as an agent for wound treatment and/or wound disinfecting and/or wound cleansing. The use of the agent for wound dressing according to the invention can occur, for example, by using the composition in conjunction with a wound dressing, preferably a bandage, a plaster, and/or some other wound covering.

For example, the composition is thus an intelligent system solution for therapeutic medicinal products in infection control, especially antimicrobial wound dressings and rinses to hasten treatment of secondary healing wounds. Benefits in regard to the hastened wound healing include the prevention of infection and the avoidance of resistance. The mentioned risk factors of silver ions are avoided. Furthermore, it is possible according to the invention to provide a new kind of dispensing system based on a carrier matrix. This enables "slow release" preparations, since the wound is stabilized in a desirable moist environment. At the same time, thanks to a depot effect of the antimicrobial composition, the wound antisepsis is optimized, without negatively affecting the wound healing.

Thanks to the astonishing skin tolerability, the use of the composition according to the invention can furthermore occur for treatment or prevention of infections, for disinfecting, or for disinfective cleansing.

The use of the composition in another embodiment is therefore possible both for skin and hand disinfecting and for disinfective cleansing. Surprisingly, besides DNA breakdown, the composition also exhibits strong activity against bacteria, mycobacteria, viruses, fungi, yeasts, prions and spores. The unexpected skin tolerability in consideration of the DNA breakdown of germs make possible for the first time an application both in skin disinfectants and in hand disinfectants, as well as cosmetic skin and hand cleansing and treatment products.

The composition can be used both as an agent for cosmetic or disinfecting and as an agent for medicinal or therapeutic treatment. In cosmetic treatment, for example, a use is possible in creams, lotions, gels or salves for applying to the skin or the hands. In particular, in skin care products for treatment of acne, in skin protection salves or products for rubbing into the skin after shaving (aftershave lotions or solutions). In therapeutic treatment, which can overlap with cosmetic treatment, for example, in the treatment of acne, the composition can be used advantageously as an agent for wound treatment, for example, as a wound rinsing solution or wound salve. The composition is especially therapeutically suitable for the treatment of infections, such as external infections of the skin or of wounds. Prophylactically, the agent can be used to prevent the transmission of infections. When the composition is used for disinfective cleansing, it can be used as an agent for hygienic hand washing, hand cleansing or skin cleansing. Surprisingly, the composition acts both against bacteria, mycobacteria, spores, prions, yeasts and fungi and against viruses and mixed infections with these germs.

The composition can be used as an agent for medicinal or disinfective treatment in application concentration or as a concentrate. When the agent is used as a skin or hands disinfectant, it is usually used in the application concentration. When used for disinfecting of surfaces or instruments, concentrates are also prepared, which are diluted to the application concentration at the place of use. The concentrations mentioned in the context of the application each refer to the product, i.e., when they are offered as a concentrate, they refer to the concentrate and not to the diluted application solution.

In an especially advantageous embodiment of the use according to the invention, the composition can be used in conjunction with a wound dressing, preferably a bandage, a plaster, and/or some other wound covering. For example, the composition can be applied in the form of a salve or a powder to a suitable carrier material. Alternatively or additionally, however, the composition can also be introduced into an intermediate layer or a self-enclosed layer of the wound dressing. It is also especially advantageous to impregnate the wound dressing, particularly the layers that come into contact with the wound, with the composition.

The composition in advantageous embodiment of the use according to the invention can also be used in dissolved form, preferably as a wound rinsing solution or moisture component of a wound dressing.

In another advantageous embodiment of the use according to the invention, the composition can furthermore be used in pastelike and/or semisolid form, preferably as a cream, gel, or salve.

Especially advantageous uses of the composition can also be realized in solid and/or dried form, wherein the composition can preferably be used as powder, tablet, granule or impregnation.

In another advantageous embodiment of the use according to the invention, the composition can be used in liquid and/or dissolved form, as a foam, solution, concentrate, emulsion, suspension or dispersion.

The composition used contains the components preferably in the following amounts:

1 mM to 1000 mM of vitamin, especially preferably 1 mM to 500 mM, even more preferably 1 mM to 300 mM and especially 1 mM to 100 mM, 0.1 mM to 100 mM of metal ion, preferably 0.4 mM to 50 mM, especially 1 mM to 30 mM, especially preferably 1 mM to 10 mM, 0.1 wt. % to 35 wt. % of surfactant, preferably 0.2 wt. % to 30 wt. %, especially 0.5 wt. % to 20 wt. %, most particularly 0.5 wt. % to 15 wt. %.

The composition used according to the invention furthermore preferably has a pH value in the range of 0.5 to 8.5, especially one of 1 to 7 and preferably one of 2 to 6 or 2 to 4.5.

The problem is solved furthermore by a therapeutic agent and/or disinfectant comprising at least one active ingredient and the usual substrates and/or adjuvants, and wherein the active ingredient is a composition that consists of at least one vitamin, at least one metal ion and at least one surfactant substance. The agent according to the invention has all essential advantages of the above-mentioned antimicrobial systems, without having their drawbacks, and furthermore it has the additional benefit of efficient removal of nucleic acids and/or proteins with relevance for infectiousness and pathogenicity.

The agent according to the invention is a three-component system, wherein two of the components in a synergistic reaction provided for an efficient breakdown of nucleic acids (DNA/RNA) and the third component transports this active complex specifically to the site of action (pathogen cells, previously damaged human cells). The breakdown of the genetic material ultimately results in killing the pathogen cells or the previously damaged (infected) human cells. Undamaged human tissue is surprisingly not attacked or adversely influenced by the agent according to the invention. The attribute of the agent according to the invention of being active even against multiresistance pathogen strains thanks to its mechanism of action and not allowing any further development of resistance clearly reveals the therapeutic and economic benefit of the agent. The agent of the invention prevents the development and transmission of resistance. In this way, for example, multiresistant strains are reduced and checked in chronic wounds and such germs are prevented from spreading contagion in hospitals, old age homes, and other facilities (the problem of MRSA). The agent of the invention is even active under heavy burdens. There is a quick killing of wound germs in a wound dressing or directly in the wound. The problem of oligodynamism, as with silver ions, is thus obviated. The agent of the invention acts selectively on pathogen cells and previously damaged human cells, while intact tissues are not harmed. Besides the breakdown of nucleic acids, the invented agent also exhibits a bactericidal action, not attributable merely to the DNA breakdown. Despite its bactericidal action and ability to break down nucleic acids, the invented agent is neither mutagenic nor cytotoxic and it exhibits a good toleration for skin and mucous membrane.

The agent according to the invention is a composition comprising three components, all of which are well characterized, they are entirely harmless in chemical and toxicological respect, they show no mutagenic potential, even in combinations, they not only kill the pathogenic germs but also destroy their genetic material (DNA/RNA), and they do not harm healthy human cells (even mucous membrane cells). Thanks to these properties, and especially the ability of the agent to specifically break down the genetic material of the pathogens (DNA/RNA), it is not possible for resistance to occur and spread in the wound germs.

Especially advantageous is the fact that the agent of the invention acts with essentially the same efficiency in the entire pH range of 0.5 to 8.5. In an advantageous embodiment of the invention, it is provided that the composition has a pH value in the range of 1 to 7, preferably 2 to 6, especially preferably 2 to 4.5. In these pH ranges, the agent of the invention is stable over a lengthy period of time and enables an especially effective breakdown of nucleic acids.

Furthermore, the skin toleration of the invented agent is optimal in the pH range of 4 to 6. This enables, in particular, a use of the disinfecting or medicinal agent for skin and hands disinfecting.

Especially preferred is one advantageous embodiment in which the composition additionally comprises a buffer system with carbonates and derivates of succinic acid, preferably each time in a concentration of 1 mM to 500 mM. When this buffer system is used in the agent of the invention, the pH value of the solution, which is in the strongly acidic region on account of the dissolved components, especially the acidic vitamins, can be easily raised to the neutral or slightly basic region, for example, without the dissolved metal ions becoming precipitated. Suitable systems include borate, oxalate, phthalate, glycine, tartrate, phosphate, carbonate, citrate and acetate buffers.

In one preferred embodiment of the invented agent, the vitamins or their salts or acid derivates are one or more compounds and/or salts thereof chosen from the group of water-soluble vitamins with properties of antioxidants, such as preferably vitamin C, riboflavin, and niacin. They are used preferably in quantities of 1 mM to 1000 mM, especially in quantities of 1 mM to 500 mM, preferably in quantities of 1 mM to 300 mM, especially preferably in quantities of 1 mM to 100 mM.

In another preferred embodiment of the agent according to the invention, the metal ions are 2 and/or 3-valent ions of metals of the 4th period and/or secondary groups I, II and VIII of the Periodic Table of Elements. They are used in the form of their salts with organic and/or inorganic acids or bases. According to the invention, one or more compounds are preferably selected from secondary group VIII, especially iron, cobalt, nickel, copper or zinc. The metal ions are preferably used in quantities of 0.1 mM to 100 mM, preferably 0.4 mM to 50 mM, especially in quantities of 1 mM to 30 mM, especially preferably in quantities of 1 mM to 10 mM.

The surfactants contained according to the invention can be, for example, anionic, nonionic, amphoteric or cationic surfactants or suitable compositions with each other or among each other. In particular, alkyl ether sulfates, alkyl and/or aryl sulfonates, alkyl sulfates, amphosurfactants, betaines, alkylamidoalkylamines, alkyl-substituted amino acids and/or imino acids, acylated amino acids and/or amphosurfactant combinations can be used. Basically all surfactants are suitable. According to the invention, anionic and nonionic surfactants are preferred. Especially preferred are natural or nature-analogous detergents. They are used preferably in quantities of 0.1 wt. % to 35 wt. %, preferably in quantities of 0.2 wt. % to 30 wt. %, especially in quantities of 0.5 wt. % to 20 wt. %, most especially in quantities of 0.5 wt. % to 15 wt. %.

The concentrations pertain each time to the composition such as is prepared as a therapeutic, disinfecting or cosmetic agent. The described concentrations thus refer to the application solution. Only the disinfectants for disinfecting of surfaces and instruments form an exception here, for which the aforementioned concentrations refer to the concentrate and not to the diluted application solution. Surface and instrument disinfectants are usually produced and marketed as concentrates. The user then carries out a dilution of these concentrates in dilution ranges between 0.25 wt. %-20 wt. %, preferably 0.5 wt. %-15 wt. %, especially preferably 0.5 wt. %-10 wt. % of the original concentrate.

The agent of the invention can additionally contain other substances, such as suitable buffers to adjust a particular pH value, like Tris (tris(hydroxymethyl)aminomethane), MES (2(morpholino)ethane sulfonic acid), HEPES (2-[4-(2-hydroxyethyl)-1-piperazinyl]ethane sulfonic acid and/or MOPS (3-(N-morpholino)-propane sulfonic acid. These buffers are used in quantities of 1 mM to 500 mM.

One wound dressing according to the invention comprises at least one carrier matrix, which is associated with the agent according to the invention. The agent according to the invention can be applied to the carrier matrix in the form of a salve or a powder.

Alternatively or additionally, however, the composition can also be introduced into an intermediate layer or a self-enclosed layer of the carrier matrix of the wound dressing. It is also especially advantageous to impregnate the carrier matrix with the composition of the invention. The carrier matrix can be, for example, a bandage material, gauze, fleece, or other material suitable for placement on wounds.

DESCRIPTION OF ADVANTAGEOUS AND PREFERRED EMBODIMENTS OF THE INVENTION

The invention shall be explained more closely by the following figures, examples and tables.

FIG. 1 shows the efficient breakdown of genomic DNA and extrachromosomal genes in microorganisms by the agent according to the invention (M: marker 1 Kb conductor; K: control with H2O; 1: 70% ethanol; 2: 0.5% Bacillozid™; 3: 0.5% SDS; 4: 0.5% sodium azide+0.5% SDS; 5: 100 mM vitamin C+10 mM $FeCl_3$+0.5% SDS; K: control: 5 µl sterile H2O).

FIG. 1 shows the efficient breakdown of genomic DNA and extrachromosomal genes in microorganisms by the agent according to the invention.

A recombinant *Escherichia coli* strain with an extrachromosomal plasmid (Yep351) was cultivated overnight in LB amp medium. Every 5 µl of this *E. coli* suspension were treated with 5 µl of lysozyme solution (1 mg/ml) for 5 minutes and then incubated for another 5 minutes with 5 µl of the indicated solutions (1-5). After adding bromophenol blue, the samples were placed in the gel bags and the DNA molecules were separated by electrophoresis. On in sample 5 with the agent of the invention (100 mM vitamin C+10 mM $FeCl_3$+ 0.5% SDS) is a massive degradation of the DNA molecules detectable. In the control with sterile water (K) and in sample 3 and 4 a lysis of the cells is observed, so that the extrachromosomal plasmid DNA is released and can migrate into the gel. In samples 1 and 2 one observes a precipitation of the cell lysate and the DNA, so that all DNA molecules remain present in the gel bag.

Table 1 shows a test for the antimicrobial action of the agent according to the invention.

Fresh cultures of the indicated microorganisms were adjusted to a cell count of 106 in 50 µl and then mixed in a 1:1 ratio with 50 µl of water 70% ethanol or the invented agent (100 mM ascorbic acid, 10 mM $FeCl_3$, and 0.5% SDS). After an incubation time of 2 minutes, the 100 µl batches with the bacteria were plated out on corresponding growth dishes. After an incubation of 1-3 days at 28° C. (*Saccharomyces cerevisiae* and *Candida parapsilosis*) or 37° C. (*Escherichia coli* and *Bacillus subtilis*), the number of grown colonies was determined. In the batches with sterile water, all microorganisms survived. The batches with 70% ethanol or the invented agent showed no colony growth, which indicates that all microorganisms had been killed in these cases.

TABLE 1

Test for the antimicrobial action of the invented agent.

| Microorganisms | H2O | 70% ethanol | therapeutic/ cosmetic agent |
|---|---|---|---|
| *Escherichia coli* | $10^6$ | 0 | 0 |
| *Bacillus subtilis* | $10^6$ | 0 | 0 |
| *Saccharomyces cerevisiae* | $10^6$ | 0 | 0 |
| *Candida parapsilosis* | $10^6$ | 0 | 0 |

Antimicrobial/Antiviral Action:

Test strains of *S. aureus, P. aeruginosa, E. hirae* and *E. coli* were reduced by a factor >$10^6$ within 15 seconds in suspension experiments. Tests with poliovirus prove the antiviral action of the invented agent. In loading tests in the disinfecting range, where the action of the invented agent was tested while adding serum protein and/or sheep erythrocytes, it was likewise possible to detect the antimicrobial and antiviral action of the agent. Thus, the invented agent also works in presence of wound secretions, blood and other organic contaminants.

Besides the above-described test, other tests were carried out on the antimicrobial action of the invented medium. The results of the tests are presented in Table 2 and 3. The disinfectants according to the invention were composed each time in the described compositions of metal salt, vitamin and surfactant and prepared as an aqueous solution. The solutions so obtained were diluted to the indicated application concentration (Conc.). Tests on the activity of the invented disinfectant were then carried out against the bacteria *S. aureus, P. aeruginosa, E. coli, Proteus mirabilis*. The measurements were taken at various bacterial loads and each time a determination was made of the reduction factor after 15 seconds, 30 seconds and 60 seconds.

acids. Thus, the agent can easily be used for both skin disinfecting and hand disinfecting. Based on the high activity, an application is also possible during disinfective cleansing, such as cosmetic or hygienic washing of the hands, when there is a low concentration present in the product. Thus, both a disinfecting of healthy skin or mucous membrane and a disinfecting in the wound area or in the area around a wound, or diseased skin or mucous membrane, is possible.

Moreover, in additional tests the antiviral action of the invented agent was investigated. For this, the reduction factors were measured after one minute, 15 minutes and 60 minutes. The activity was determined against the Polyoma

TABLE 2

Compositions and recipes of the invented disinfectant and results of measurements of the reduction factor under load with respect to *P. aeruginosa*.

| Recipe No | M salt (in mM) $FeCl_3 \cdot 6H_2O$ | "vitamin" (in mM) D-ascorbic acid | surfactant (in %) SDS | water | Conc. [%] | load | *Ps. aeruginosa* (Gram-negative) 15" | 30" | 60" |
|---|---|---|---|---|---|---|---|---|---|
| A | 10 | 100 | 0.5 | ad 100.0 | 50.0 | clean | >6.48 | >6.48 | >6.48 |
| B | 1 | 10 | 0.5 | ad 100.0 | 50.0 | clean | 4.74 | 5.36 | >6.34 |

TABLE 3

Compositions and recipes of the invented disinfectant and results of measurements of the reduction factor under load with respect to *Proteus mirabilis*.

| Recipe No. | M salt (in mM) $FeCl_3 \cdot 6H_2O$ | $FeSO_4 \cdot 7H_2O$ | "vitamin" (in mM) D-ascorbic acid | surfactant (in %) SDS | polysorbate 20 Tween 20 | water | Conc. [%] | load | *Proteus mirabilis* (Gram-positive) 15" | 30" | 60" |
|---|---|---|---|---|---|---|---|---|---|---|---|
| C | 1 | | 10 | 0.5 | | ad 100.0 | 50.0 | clean | >6.40 | >6.40 | >6.40 |
| D | | 10 | 100 | 0.5 | 0.3 | ad 100.0 | 50.0 | clean | >6.31 | >6.31 | >6.31 |

The measurements of the antibacterial action of the agent according to the invention show that this displays a good bactericidal action, besides an efficient breakdown of nucleic and Vaccinia virus. The composition of the respective test solutions and the results of the values are reflected in the following Table 4 and 5.

TABLE 4

Compositions of the invented disinfectant and results of measurements of the reduction factors with respect to Polyoma.

| Recipe No. | M salt (in mM) $FeCl_3 \cdot 6H_2O$ | $CuCl_2$ | "vitamin" (in mM) D-ascorbic acid | surfactant (in %) SDS | polysorbate 20 Tween 20 | water | Conc. [%] | load | Polyoma (nonenveloped virus) 1' | 15' | 60' |
|---|---|---|---|---|---|---|---|---|---|---|---|
| E | | 6.25 | 62.5 | 1.0 | | ad 100.0 | 80.0 | none | 5.55 | >5.67 | >5.67 |
| F | 1.25 | | 12.5 | 0.625 | 0.375 | ad 100.0 | 80.0 | none | 5.50 | 5.50 | 6.50 |

TABLE 5

Compositions of the invented disinfectant and results of measurements of the reduction factors with respect to Vaccinia.

| Recipe No. | M salt (in mM) | | "vitamin" (in mM) | surfactant (in %) polysorbate 20 | | | | | Vaccinia (enveloped virus) | | |
|---|---|---|---|---|---|---|---|---|---|---|---|
| | FeCl$_3$x6H2O | ZnCl$_2$ | D-ascorbic acid | SDS | Tween 20 | water | Conc. [%] | load | 1' | 15' | 60' |
| G | 12.50 | | 125.0 | 0.625 | 0.375 | ad 100.0 | 80.0 | none | 6.67 | 6.67 | 6.67 |
| H | | 1.25 | 12.5 | 1.0 | | ad 100.0 | 80.0 | none | 6.33 | 6.33 | 6.33 |

The tests revealed that the agents according to the invention display surprisingly good antiviral effects, besides the breakdown of nucleic acids and the good antibacterial effects. Thus, a very good reduction was observed with respect to all viruses tested, even after short exposure times.

Moreover, additional tests showed that the agent of the invention also has a high activity against fungi and yeasts. Thus, in summary, it can be said that the measurement results show that the agents according to the invention, with good skin toleration, also exhibit a large activity against bacteria, mycobacteria, viruses, fungi, yeasts, prions and spores, besides the nucleic breakdown. Therefore, the agent according to the invention can be applied successfully in areas where a load with different germs occurs and a reduction of various germ species is desired.

Skin Toleration:

Extensive data on the individual ingredients of the agent according to the invention show its generally good skin toleration. The agent according to the invention employs only ingredients or substances that are already being used individually in the most diverse of forms in cosmetics, nutrients, nutritional supplements, medicinal products and pharmaceuticals. Initial tests with the agent according to the invention, i.e., the combination of vitamin, metal ion and detergents, also revealed no undesirable skin changes.

Biocompatibility:

The agent according to the invention was tested in the highest concentrations in the Bruce-Ames test for mutagenicity. No mutagenic potential could be found. Also, in the activated Bruce-Ames test with liver cell extracts, no mutagenicity was displayed. In initial tests of the agent according to the invention on the chicken egg model, likewise no harmful influences on the development could be found.

Material Compatibility:

Besides skin toleration, a good material compatibility is also important in the use of the agent according to the invention. Measurements of the material compatibility with regard to polyethylene, polypropylene, polycarbonate, PMMA, polystyrene, PTFE, PVC, silicone, latex and Viton revealed a good material compatibility. Thus, an application of the disinfectant is also possible as an agent for disinfecting of surfaces or instruments.

The invention claimed is:

1. A method to effect breakdown of DNA and/or RNA of pathogens present at is site of a wound or infection, comprising, administering to a wound on a human or animal body or to infections of the mucous membrane a composition consisting essentially of at least one vitamin, at least one metal ion and at least one surface-active substance,
    under conditions that effect breakdown of DNA and/or RNA of pathogens present at the site of the wound or infection.

2. The method according to claim 1, in which the composition is effective for wound treatment and/or wound disinfection and/or wound cleaning.

3. The method according to claim 1, in which the composition is used in combination with a compress or wound overlay.

4. The method according to claim 1, in which the composition comprises the vitamin in amounts of 1 mM to 1000 mM and/or the metal ion in amounts of 0.1 mM to 100 mM and/or the surface-active substance in amounts of 0.1 wt % to 35 wt % and/or the composition has a pH in the range of 0.5 to 8.5.

5. The method according to claim 1, in which the composition is used in dissolved or foamed form.

6. The method according to claim 1, in which the composition is used in pasty and/or semisolid form.

7. The method according to claim 1, in which the composition is used in solid and/or dry form.

8. The method according to claim 1, in which the composition is present in liquid and/or dissolved form.

9. The method according to claim 3, wherein the compress or wound overlay is a bandage, a plaster and/or wound covering.

10. The method according to claim 6, wherein the pasty and/or semisolid form is a crème, gel or salve.

11. The method according to claim 5, wherein the dissolved or foamed form is a wound rinse solution or moist component of a wound overlay.

12. The method according to claim 7, wherein the solid and/or dry form is a powder, granulate, tablet or impregnation.

13. The method according to claim 8, wherein the liquid and/or dissolved form is a solution, concentrate, emulsion, dispersion, foam or suspension.

14. The method according to claim 1, wherein the ratio of the at least one metal ion to the at least one vitamin is 1:10.

* * * * *

UNITED STATES PATENT AND TRADEMARK OFFICE
CERTIFICATE OF CORRECTION

| | | |
|---|---|---|
| PATENT NO. | : 8,557,265 B2 | Page 1 of 1 |
| APPLICATION NO. | : 12/452295 | |
| DATED | : October 15, 2013 | |
| INVENTOR(S) | : Krug et al. | |

It is certified that error appears in the above-identified patent and that said Letters Patent is hereby corrected as shown below:

On the Title Page

Item (75) column 1, two inventors' names are misspelled, although they were correctly spelled in the Declaration.

Please change "Frank Büger" to -- Frank Bürger --
Please change "Richard Bloss" to -- Richard Bloß --

Signed and Sealed this
Ninth Day of June, 2015

Michelle K. Lee
*Director of the United States Patent and Trademark Office*